United States Patent
Villalobos et al.

(12) 
(10) Patent No.: US 12,357,558 B2
(45) Date of Patent: Jul. 15, 2025

(54) **TOPICAL SKINCARE COMPOSITIONS COMPRISING *CENTELLA ASIATICA***

(71) Applicant: The Procter & Gamble Company, Cincinnati, OH (US)

(72) Inventors: Janette Marie Villalobos, Miami Springs, FL (US); Jonathan Javier Calderas, Cincinnati, OH (US); Leo Timothy Laughlin, II, Mason, OH (US); Teresa Dicolandrea, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 721 days.

(21) Appl. No.: 17/531,843

(22) Filed: Nov. 22, 2021

(65) Prior Publication Data

US 2022/0079870 A1 Mar. 17, 2022

Related U.S. Application Data

(63) Continuation of application No. PCT/US2019/041760, filed on Jul. 15, 2019.

(51) Int. Cl.
*A61K 8/9789* (2017.01)
*A61K 8/06* (2006.01)
*A61Q 19/00* (2006.01)

(52) U.S. Cl.
CPC .............. *A61K 8/9789* (2017.08); *A61K 8/062* (2013.01); *A61Q 19/00* (2013.01); *A61K 2800/30* (2013.01); *A61K 2800/524* (2013.01); *A61K 2800/591* (2013.01)

(58) Field of Classification Search
None
See application file for complete search history.

(56) References Cited

U.S. PATENT DOCUMENTS

| | | |
|---|---|---|
| 6,261,603 B1 | 7/2001 | Mcelwain |
| 9,050,359 B2 | 6/2015 | Yesudas et al. |
| 9,889,174 B2 | 2/2018 | Yesudas et al. |
| 2008/0279902 A1 | 11/2008 | Luria et al. |
| 2013/0149398 A1 | 6/2013 | Yesudas et al. |
| 2021/0205386 A1 | 7/2021 | Osorio et al. |
| 2022/0184169 A1 | 6/2022 | Yesudas et al. |

FOREIGN PATENT DOCUMENTS

| | | | |
|---|---|---|---|
| CN | 1049122 C | 2/2000 | |
| CN | 1516593 A | 7/2004 | |
| CN | 103110917 A | 5/2013 | |
| CN | 103687606 A | 3/2014 | |
| CN | 104940378 A | 9/2015 | |
| CN | 108938957 A | 12/2018 | |
| JP | 2008184441 A | 8/2008 | |
| KR | 20100121066 A | 11/2010 | |
| KR | 20150050983 A | 5/2015 | |
| WO | WO-9739734 A1 * | 10/1997 | ............ A61K 8/42 |
| WO | 03047609 A1 | 6/2003 | |
| WO | 2013106068 A2 | 7/2013 | |
| WO | 2017091764 A1 | 6/2017 | |

OTHER PUBLICATIONS

PCT Search Report and Written Opinion for PCT/US2019/041760 dated Mar. 16, 2020, 15 pages.

* cited by examiner

*Primary Examiner* — Susan Hoffman
(74) *Attorney, Agent, or Firm* — Alexandra S. Anoff

(57) ABSTRACT

The present disclosure relates to a topical skincare composition comprising a *Centella asiatica* extract in combination with a *Vincetoxicum officinale* extract and/or a *Populas alba* extract. The present disclosure further relates to methods of treating symptoms of itch, redness, flaking, dryness, and/or roughness of the skin, scalp, and/or mucous membrane using such topical skincare compositions.

9 Claims, No Drawings

TOPICAL SKINCARE COMPOSITIONS COMPRISING *CENTELLA ASIATICA*

FIELD OF THE INVENTION

The present disclosure relates to a topical skincare composition comprising a *Centella asiatica* extract in combination with a *Vincetoxicum officinale* extract and/or a *Populas alba* extract. The present disclosure further relates to methods of treating symptoms of itch, redness, flaking, dryness, and/or roughness of the skin, scalp, and/or mucous membrane using such topical skincare compositions.

BACKGROUND OF THE INVENTION

Challenged skin conditions such as eczema and psoriasis can prove to be frustrating and a nuisance to those who suffer from them. Symptoms of eczema and/or psoriasis may include itch, redness, flaking, dryness, and/or roughness. Itch, redness, flaking, dryness, and/or roughness can occur for a variety of reasons, for instance, in response to an environmental trigger such as cold weather, or an immune trigger such as an allergen response. Such skin conditions may be acute in nature (i.e., occur in a singular, independent incidence) or may be more chronic (i.e., affect the individual for a prolonged period of time). When symptoms of challenged skin occur, the person suffering from the condition generally wishes to alleviate the symptoms as quickly as possible. However, challenged skin may be more sensitive and prone to irritation.

Prescription and over-the-counter steroids can be very effective in relief of symptoms associated with challenged skin. However, it is known that prolonged exposure to steroids may have local and systemic side effects which may include skin atrophy or thinning, telangiectasia, stretch marks, acne, folliculitis, and bruising. Thus instead of using steroids for long-term management, many consumers turn to topical moisturizers.

Topical moisturizers can be an effective adjunct treatment for the long-term management of challenged skin conditions in improving skin health. However, while many moisturizers aim to maintain healthy skin over long-term application, moisturizers are not known to provide fast and/or sufficient relief for those experiencing symptoms of challenged skin. A person experiencing a flare might apply moisturizer and then when the itch, redness, flaking, dryness, and/or roughness is not alleviated quickly enough, the person may stop using the moisturizer in search of a faster-acting treatment, such that the skin does not experience the benefit of the long-term use of a moisturizer. The person might also scratch the affected area while waiting for relief, disrupting the skin further.

Incorporating additional ingredients to speed up relief or to address additional symptoms can be challenging for formulators as the interaction between ingredients on skin biology, especially on challenged skin, is complex and often unpredictable. Topical moisturizers are complex mixtures containing many ingredients and such ingredients can potentially cause undesirable side effects such as increased irritation and/or erythema on the portion of the user's skin to which the topical composition is applied. Users who experience such undesirable side effects might choose to not repurchase the product.

In sum, it is challenging to provide a topical skincare composition that can provide relief of uncomfortable acute and chronic symptoms of challenged skin conditions without resulting in further irritation or other undesirable side effects. Surprisingly, it has been found that a combination of a *Centella asiatica* extract, a *Populas alba* extract, and/or a *Vincetoxicum officinale* extract, along with a dermatologically acceptable carrier, can provide for relief of symptoms of challenged skin conditions as well as being acceptable for long-term use and improving skin health without the trade-off of increased irritation and other undesirable side effects.

SUMMARY OF THE INVENTION

The present disclosure relates to a topical skincare composition comprising: a *Centella asiatica* extract; a *Populas alba* extract; and a dermatologically acceptable carrier, wherein the *Centella asiatica* extract and the *Populas alba* extract are in a weight ratio of about 1:5 to about 1,000:1.

The present disclosure also relates to a topical skincare composition comprising: a *Centella asiatica* extract; a *Vincetoxicum officinale* extract; and a dermatologically acceptable carrier, wherein the *Centella asiatica* extract and the *Vincetoxicum officinale* extract are in a weight ratio of about 1:2 to about 100:1.

The present disclosure further relates to a method of treating symptoms of itch, redness, flaking, dryness, and/or roughness of the skin, scalp, and/or mucous membrane, the method comprising the steps of: providing a topical skincare composition comprising a *Centella asiatica* extract in combination with a *Vincetoxicum officinale* extract and/or a *Populas alba* extract, and a dermatologically acceptable carrier; and applying a safe and effective amount of the topical skincare composition to at least a portion of a user's skin, scalp, and/or mucous membrane in need thereof.

DETAILED DESCRIPTION OF THE INVENTION

Definitions

As used herein, the articles "a" and "an" when used in a claim, are understood to mean one or more of what is claimed or described. As used herein, the terms "include," "includes," and "including" are meant to be nonlimiting.

As used herein, the terms "components", "ingredients", and "materials" may be used interchangeably unless otherwise specified.

As used herein "cosmetic agent" means any substance, as well as any component thereof, intended to be rubbed, poured, sprinkled, sprayed, introduced into, or otherwise applied to a mammalian body or any part thereof to provide a cosmetic benefit. Cosmetic agents may include substances that are Generally Recognized as Safe (GRAS) by the United States Food and Drug Administration, food additives, and materials used in non-cosmetic consumer products including over-the-counter medications. A cosmetic agent may include, but is not limited to, (i) chemicals, compounds, small or large molecules, extracts, formulations, or combinations thereof that are known to induce or cause at least one effect (positive or negative) on skin tissue; (ii) chemicals, compounds, small molecules, extracts, formulations, or combinations thereof that are not known have an effect on skin tissue and are discovered, using the provided methods and systems, to induce or cause an effect on skin tissue; and (iii) a compound or combination of compounds that, when applied to skin, provide an acute and/or chronic benefit to skin or a type of cell commonly found therein. Cosmetic agents may regulate and/or improve skin or its associated cells (e.g., improve skin elasticity; improve skin hydration; improve skin condition; and improve cell metabolism).

As used herein, the terms "irritation", "inflammation", "itch", "redness", "burning", "stinging", and "pain" refer to undesirable sensory perceptions, noticeable to a human subject able to report them or measurable by ion channel activation or comparable analytical methodology.

As used herein, the term "topical application" means to apply or spread the compositions of the present disclosure onto the surface of the skin.

The phrase "dermatologically acceptable carrier", as used herein, means that the carrier is suitable for topical application to the keratinous tissue without undue toxicity, incompatibility, instability, allergic response, and the like, has good aesthetic properties, and is compatible with any additional components of the skincare composition.

As used herein, the term "dermatitis" means a condition of the skin in which the skin becomes red, swollen, and/or sore, sometimes with small blisters, resulting from direct irritation of the skin by an external agent or an allergic reaction to it. Examples of dermatitis include, but are not limited to, eczematous dermatitis, contact dermatitis, atopic dermatitis, and/or seborrheic dermatitis.

As used herein, the term "atopic dermatitis" ("AD") is a multifactorial chronic inflammatory skin disorder characterized by genetic barrier defects and allergic inflammation, which is sustained by gene-environmental interactions. AD may be characterized by pruritic and eczematous skin lesions with erythema, excoriation, erosions, lichenification and dryness, frequently accompanied by increased serum immunoglobulin E (IgE) levels. Those with AD may experience areas of severe itching, redness, scaling, and loss of the surface of the skin. AD is a disease arising from the complex interactions between multiple factors, like genetic background, immunologic abnormalities and exposure to environmental sensitizers or allergens. Among these, the dysfunction and breakdown of skin barrier is suggested as an important contributor to the development of AD. The patients with AD generally exhibit xerotic skin resulting from impaired epidermal barrier and the impaired skin barrier function allows the facile penetration of allergens and subsequently stronger sensitization responses, indicating that skin barrier dysfunction plays a critical role in the aggravation and the flares of AD.

As used herein, the term "dermatosis" means a noninflammatory disorder of the skin.

As used herein, the term "keratinous tissue", refers to keratin-containing layers disposed as the outermost protective covering of mammals which includes, but is not limited to, skin, hair, nails, cuticles, etc.

As used herein, the terms "plant extract" or "natural extract" or "extract" with reference to a plant is any material extracted from natural resources including plants. The entire plant or any part of the plant including the bark, berries, flowers, leaves, stem, stalk, peels, resins, rhizome, roots, seeds, woods and mixtures thereof may be used for the extraction process. Extracts may be obtained using any suitable method known in the art including: milling, grinding, maceration, infusion, percolation and decoction, Soxhlet extraction, microwave assisted extraction, ultrasound-assisted extraction, sonication extraction, solvent extraction, accelerated solvent extraction, and supercritical fluid extraction. Suitable extraction solvents may include water, ketones, esters, $C_1$ to $C_6$ alcohols, hydrocarbons and mixtures thereof.

As used herein, the term "safe and effective amount" means an amount of a material, ingredient, compound, component, or composition sufficient to significantly induce a positive benefit, but low enough to avoid serious side effects such as undue toxicity or allergic reaction.

As used herein, the term "skin" means the outermost protective covering of mammals that is composed of cells such as keratinocytes, fibroblasts and melanocytes. Skin includes an outer epidermal layer and an underlying dermal layer. Skin may also include hair follicles, sebaceous gland layer and nails as well as other types of cells commonly associated with skin, such as, for example, myocytes, Merkel cells, Langerhans cells, macrophages, stem cells, sebocytes, nerve cells and adipocytes.

As used herein, the term "actives", with reference to skincare, means compounds that, when applied to the skin, provide a benefit or improvement to the skin. It is to be understood that skincare actives are useful not only for application to skin, but may also be useful to hair, nails and other mammalian keratinous tissue.

As used herein, the terms "sensitive skin", "hypersensitive skin", and "challenged skin" may include irritable skin and intolerant skin. As used herein, "irritable skin" means skin that reacts through pruritus, i.e., through itching or stinging, to various factors such as the environment, emotions, foods, the wind, rubbing, shaving, hard water with a high calcium or other element concentration, temperature variations, humidity, or wool. As used herein, "intolerant skin" means skin that reacts to various factors, such as the application of cosmetic or dermatological products or soap, through sensations of overheating, tautness, pins and needs, and/or redness.

The terms "substantially free of" or "substantially free from" may be used herein. This means that the indicated material is at the very minimum not deliberately added to the composition to form part of it. The indicated material may be present, if at all, at a level of less than about 0.5%, or less than about 0.01%, or less than about 0.0001%, or less than about 0.000001%, or even 0%, by weight of the composition.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C., under atmospheric pressure, and at 50% relative humidity.

In the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Active and other ingredients useful herein may be categorized or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefore, classifications herein are made for the sake of convenience and are not intended to limit an ingredient to the particularly stated application or applications listed.

Applicant has found that topical skincare compositions of the present disclosure may provide visual and/or therapeutic improvement and/or relief in the skin, scalp, and/or mucous membrane following application of the topical skincare composition and further may be non-irritating to the skin, scalp, and/or mucous membrane.

Without wishing to be bound by theory, Applicant has found that *Centella asiatica* extract may reduce skin irritation caused by an external stimulus by reducing the release of Prostaglandin E2 (PGE2), an inflammatory mediator. And, compositions comprising a mixture of plant extracts obtained from at least two plants selected from the group consisting of: *Achillea millefolium*; *Aesuculus hippocastanum*; *Althaea officinalis*; *Avena sativa*; *Berberis vulgaris*; *Capsella bursa pastoris*; *Cochlearia officinalis*; *Conium maculatium*; *Ervum lens*; *Hamamelis virginiana*; *Hydrastis canadensis*; *Matricaria chamomilla*; *Nasturtium officinale*; *Phytolacca decendra*; *Pimpinella saxifraga*; *Populas alba*; *Populus tremuloides*; *Rhus toxicodendron*; *Sambucus nigra*; *Sanguinaria canadensis*; *Scrophularia nodosa*; *Smilax medica*; *Tussilago farfara*; *Veronica officinalis*; and *Vincetoxicum officinale*, for the treatment of skin conditions are known. However, Applicant has surprisingly found that although *Centella asiatica* extract alone may be capable of reducing the potential for irritation, the addition of *Populas alba* extract and/or *Vincetoxicum officinale* extract to *Centella asiatica* extract may provide a synergistic benefit of a reduction in skin itch and irritation.

I. Topical Skincare Compositions

Topical skincare compositions of the present disclosure may be applied to mammalian keratinous tissue, in particular to human skin. The topical skincare compositions disclosed herein may be useful for providing relief of challenged skin symptoms following application of the composition to the skin. The topical skincare compositions useful in the subject disclosure may be made into a wide variety of product forms such as are known in the art. These may include, but are not limited to, creams, lotions, serums, sprays, tonics, gels, solutions, suspensions, aerosol sprays, sticks, ointments, liquid washes, soap bars, shampoos, hair conditioners, pastes, foams, powders, mousses, shaving creams, hydrogels, film-forming products, and the like. The topical skincare composition form may follow from the particular dermatologically acceptable carrier chosen.

In a non-limiting example, the topical skincare composition may be substantially free of a steroid. While topical and oral steroid therapies are frequently used to provide relief of such symptoms, they do not restore the structure of the lamellar body and lipid bilayer in the lower stratum corneum, which constitute the epidermal barrier function. Preferably, the topical skincare composition may be free of a steroid, or comprise 0%, by weight of the composition, of a steroid. Nonlimiting examples of steroids may include but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

*Centella asiatica* Extract

The topical skincare composition may comprise at least 0.000001%, preferably from about 0.00001% to about 5%, more preferably from about 0.0001% to about 1.5%, even more preferably from about 0.001% to about 1.5%, by weight of the composition, of a *Centella asiatica* extract. The *Centella asiatica* plant, may also be known as Violette marronne (on Reunion Island), Gotu Kola or Indian pennywort (in India), *Centella repanda* (in North America), Tiger Grass, and Talapetraka (in Madagascar). The *Centella asiatica* extract may comprise one or more triterpenes, wherein at least one of the one or more triterpenes is madecassic acid.

Triterpenes are groups of terpenes found in plant gums and resins, having unsaturated molecules based on a unit with the formula $C_{30}H_{48}$. The *Centella asiatica* plant includes the triterpenes of asiatic acid, madecassic acid, asiaticoside, and madecassoside. The biological activity of the *Centella asiatica* plant appears to be due to the presence of triterpene molecules in the plant. In a nonlimiting example, the *Centella asiatica* extract of the present disclosure may comprise two or more triterpenes selected from the group consisting of asiaticoside, asiatic acid, madecassoside, madecassic acid, and mixtures thereof. In a nonlimiting example, the *Centella asiatica* extract may comprise from about 20% to about 60%, preferably from about 30% to about 50%, by weight of the *Centella asiatica* extract, of asiaticoside. In a nonlimiting example, the *Centella asiatica* extract may comprise from about 40% to about 80%, preferably from about 50% to about 70%, by weight of the *Centella asiatica* extract, of a mixture of asiatic acid and madecassic acid.

An example of a commercially available *Centella asiatica* extract having one or more triterpenes include the products sold under the tradenames CENTEVITA™ (≥45.0% of the sum of asiaticoside, madecassoside, asiatic acid and madecassic acid; made commercially available by Indena Milan, Italy); *Centella asiatica* Selected Triterpenes (CAST) (having ≥36.0%≤44.0% of asiaticoside, ≥56%≤64.0% of genins as a sum of asiatic acid and madecassic acid; made commercially available by Indena (Milan, Italy); and Titrated Extract of *Centella asiatica* (TECA®) (INCI Name: Asiaticoside (and) Madecassic Acid (and) Asiatic Acid; made commercially available by SEPPIC (Paris, France).

*Populas alba* Extract

The topical skincare composition may comprise at least 0.000001%, preferably from about 0.00001% to about 2%, more preferably from about 0.00005% to about 1%, more preferably from about 0.0001% to about 0.1% by weight of the composition, of a *Populas alba* extract. *Populas alba* may also be known as white poplar, silver leaf poplar, silver poplar, or *Populas alba*.

*Populas alba* is known for use internally in the treatment of rheumatism, arthritis, gout, lower back pains, urinary complaints, digestive and liver disorders, debility, anorexia, also to reduce fevers and relieve the pain of menstrual cramps. Externally, *Populas alba* bark is known to treat chilblains, haemorrhoids, infected wounds, and sprains.

*Populas alba* bark extract is available from Spaus, Inc. (Suite 460, Oklahoma City, OK 73104).

The weight ratio of *Centella asiatica* extract to *Populas alba* extract in a composition can be about 1:5, about 1:3, about 1:2, about 1:1, about 2:1, about 5:1, about 10:1, about 20:1, about 50:1, about 100:1, about 200:1, about 500:1 or about 1,000:1.

*Vincetoxicum officinale* Extract

The topical skincare composition may comprise at least 0.000001%, preferably from about 0.000001% to about 2%, more preferably from about 0.00001% to about 1%, more preferably from about 0.0002% to about 0.1% by weight of the composition, of a *Vincetoxicum officinale* extract. *Vincetoxicum officinale* may also be known as *Cynanchum vincetoxicum*, white swallow wort, *Asclepias vincetoxicum*, German ipecac, Asclépiade Blanche, Dompte-Venin, Dompte Venin, swallow wort, vencetósigo, and *Vincetoxicum hirundinaria*.

*Vincetoxicum officinale* is known to be used for digestion problems, kidney disorders, and fluid retention.

*Vincetoxicum officinale* root extract is available from Spaus, Inc. (Suite 460, Oklahoma City, OK 73104).

In one example, the weight ratio of *Centella asiatica* extract to *Vincetoxicum officinale* extract in a composition can be about 1:2, about 1:1, about 2:1, about 3:1, about 4:1, about 5:1, about 10:1, about 20:1, about 50:1, or about 100:1.

Dermatologically Acceptable Carrier

The topical skincare composition of the present disclosure may comprise a safe and effective amount, for example, from about 50% to about 98%, preferably from about 60% to about 90%, of a dermatologically acceptable carrier ("carrier") for the composition. The carrier can thus act as a diluent, dispersant, solvent, or the like to ensure that the materials can be applied to and distributed evenly over the selected target at an appropriate concentration.

Suitable carriers may include conventional or otherwise known carriers that are dermatologically acceptable. The carrier should also be physically and chemically compatible with the actives as described herein, and should not unduly impair stability, efficacy or other use benefits associated with the compositions of the present disclosure. Preferred components of the compositions of this disclosure should be capable of being comingled in a manner such that there is no interaction which would substantially reduce the efficacy of the composition under ordinary use situations.

The dermatologically acceptable carrier may be in a wide variety of forms. Nonlimiting examples may include simple solutions (e.g., aqueous, organic solvent, or oil-based), emulsions, and solid forms (e.g., gels, sticks, flowable solids, wax, amorphous materials). Emulsions may be generally classified as having a continuous aqueous phase (e.g., oil-in water and water-in-oil-in-water) or a continuous oil phase (e.g., water-in-oil and oil-in-water-in-oil). The oil phase of the present disclosure may comprise silicone oils, non-silicone oils such as hydrocarbon oils, esters, ethers, and the like, and mixtures thereof. A suitable dermatologically acceptable carrier is selected to yield a desired product form. Furthermore, the solubility or dispersability of the components may dictate the form and character of the carrier.

The aqueous phase may typically comprise water. However, in other non-limiting examples, the aqueous phase may comprise components other than water, including but not limited to water-soluble moisturizing agents, conditioning agents, anti-microbials, humectants, and/or other water-soluble skin care actives. In a non-limiting example, the non-water component of the composition may comprise a humectant, such as glycerin, and/or other polyols. However, it should be recognized that the composition may be substantially (i.e., less than 1% water) or fully anhydrous.

For emulsions, the topical skincare composition may comprise from at least 0.001%, preferably from about 0.001% to about 15%, more preferably from about 0.1% to about 10%, more preferably from about 0.1% to about 5%, by weight of the topical skincare composition, of an emulsifier/surfactant. The composition may comprise any suitable percentage of emulsifier/surfactant to sufficiently emulsifier the dermatologically acceptable carrier. Suitable surfactants may include but are not limited to non-silicone-containing emulsifiers/surfactants, silicone emulsifiers/surfactants, and mixtures thereof. Emulsifiers/surfactants may be nonionic, anionic, or cationic. Preferred among the non-ionic surfactants are those selected from the group consisting of steareth-21, ceteareth-20, ceteareth-12, sucrose cocoate, steareth-100, PEG-100 stearate, cetearyl glucoside, cetearyl alcohol, stearic acid, and mixtures thereof. Suitable emulsifiers are disclosed in, for example, U.S. Pat. Nos. 3,755,560 and 4,421,769. Suitable emulsions may have a wide range of viscosities depending on the desired product form.

The carrier may comprise one or more dermatologically acceptable solid, semi-solid or liquid fillers, diluents, solvents, extenders and the like. The carrier may be solid, semi-solid or liquid in form. The dermatologically acceptable carrier may itself be inert or it may possess dermatological benefits of its own. Concentrations of the carrier may vary with the carrier selected and the intended concentrations of other components of which the topical skincare composition is comprised. As will be understood by one skilled in the art, a given component will distribute primarily into either the aqueous phase or oil phase, depending on the water solubility/dispersability of the component in the composition.

Lipid Bilayer Structurants

The topical skincare composition may comprise at least 0.01%, preferably from about 0.01% to about 20%, more preferably from about 0.1% to about 15%, by weight of the composition, of a lipid bilayer structurant. Lipid bilayer structurants are materials which can favorably interact with and pack the lipid bilayer allowing for improvement of its barrier function and leading to better skin hydration.

The topical skincare composition of the present disclosure may comprise a lipid bilayer structurant selected from the group consisting of batyl alcohol, glyceryl monooleate, isostearyl glyceryl ether, glyceryl isostearate, glyceryl monoerucate, glyceryl oleate, hexadecyl glyceryl ether, glyceryl monostearate, glyceryl monooleate, glyceryl monohydroxystearate, glyceryl monolinoleate, isopropyl isostearate, isopropoyl palmitate, myristyl myristate, myristyl palmitate, myristyl stearate, palmityl palmitate, cetyl stearate, stearyl stearate, isocetyl stearate, isooctadecyl palmitate, isohexadecyl isoctadecanoate, isooctadecanoic acid, 2-hydroxyoctadecyl ester, cetyl glycol isostearate, and mixtures thereof. Preferably, the lipid bilayer structurant is selected from the group consisting of batyl alcohol, isopropyl isostearate, and mixtures thereof.

Preservatives

The topical skincare composition may comprise at least 0.0001%, about 0.001%, about 0.01%, about 0.05%, about 0.1%, about 0.5%, by weight of the composition, a preservative. Preservatives are commonly used in topical skincare compositions to prevent or retard the formation of yeast, bacteria, and/or mold.

The topical skincare composition of the present disclosure may comprise a preservative selected from the group consisting of benzoic acid and salts thereof, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, sodium benzoate, calcium benzoate, calcium propionate, caprylyl glycol, biguanide derivatives, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM hydantoin, DEDM hydantoin dilaurate, dehydroacetic acid, diazolidinyl urea, dibromopropamidine diisethionate, DMDM hydantoin, glyceryl caprylate, potassium sorbate, salicylic acid, hexamidine, capryloyl glycine, 1,2-hexanediol, undecylenoyl glycine, ethylhexylglycerin, caprylhydroxamic acid, methylpropanediol, hinokitiol, sodium hinokitiol, phenylethyl alcohol, levulinec acid, p-anisic acid, 2-bromo-2-nitropipane-1,3-diol, sodium hydroxymethylglycinate, iodopropynyl bulylcarbamate, methylchloroisothiazolinone, methylisothiazolinone, piroclone olamine, cinnamon oil, rosemary extract, and combinations thereof.

Emollients

The topical skincare composition may comprise from about 0.001% to about 90%, preferably from about 0.01% to about 50%, more preferably from about 0.1% to about 30%, of the topical skincare composition, of an emollient. Emollients tend to lubricate the skin, increase the smoothness and suppleness of the skin, prevent or relieve dryness of the skin, and/or protect the skin. Emollients may physically prevent or reduce moisture loss from the skin by formation of a water-impenetrable barrier over the stratum corneum. Emollients are typically water-immiscible, oily or waxy materials. The level of emollient within the topical skincare composition, when present, may vary according to the form of the topical skincare composition.

Nonlimiting examples of emollients may include isopropyl isostearate, caprylic/capric triglycerides, petrolatum, dimethicone, dimethiconol, and mixtures thereof. The topical skincare composition may comprise an emollient selected from the group consisting of isopropyl isostearate, caprylic/capric triglycerides, petrolatum, dimethicone, dimethiconol, and mixtures thereof.

Structuring Agent

The topical skincare composition may comprise from about 0.01% to about 15%, preferably from about 0.1% to about 10%, more preferably from about 0.5% to about 5%, by weight of the composition, of a structuring agent. Structuring agents may be particularly preferred in oil-in-water emulsions. Without being limited by theory, it is believed that the structuring agent may assist in providing rheological characteristics to the composition which contribute to the stability of the composition. For example, the structuring agent tends to assist in the formation of the liquid crystalline gel network structures. The structuring agent may also function as an emulsifier or surfactant.

Nonlimiting examples of structuring agents may include stearic acid, palmitic acid, stearyl alcohol, cetyl alcohol, behenyl alcohol, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. Preferably, the topical skincare composition may comprise a structuring agent selected from the group consisting of stearic acid, palmitic acid, stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof.

Thickening Agent

Topical skincare compositions may also comprise from about 0.01% to about 10%, preferably from about 0.1% to about 5%, more preferably from about 0.2% to about 5% by weight of the topical skincare composition, of a thickening agent. The thickening agent may be provided in any amount known to one skilled in the art to facilitate achieving the desired viscosity in combination with the other ingredients in the skin care composition. Thickening agents may be used to adjust the viscosity of a composition without substantially changing its other properties. Thickening agents may also improve the suspension of other ingredients. Some thickening agents may also function as stabilizers when they are used to maintain the stability of an emulsion. Thickening agents may be especially useful in products forms such as ointments.

Non-limiting examples of thickeners that may be suitable for use herein include gums, modified gums, starches, modified starches, clays, and cross-linked water swellable polymers. Other non-limiting examples of thickeners are disclosed in U.S. Publication No. 2008/0051497 and U.S. Pat. No. 9,795,552. The topical skincare composition may comprise a thickening agent selected from the group consisting of carboxylic acid polymers, crosslinked polyacrylate polymers, polyacrylamide polymers, polysaccharides, gums, crosslinked vinyl ether/maleic anhydride copolymers, crosslinked poly(N-vinylpyrrolidones), and mixtures thereof. Preferably, the topical skincare composition may comprise a thickening agent selected from the group consisting of carboxylic acid polymers, crosslinked polyacrylate polymers, polyacrylamide polymers, and mixtures thereof, more preferably selected from the group consisting of crosslinked polyacrylate polymers, polyacrylamide polymers, and mixtures thereof.

Humectants

Topical skincare compositions may also comprise from about 1% to about 45%, preferably from about 2.5% to about 25%, more preferably from about 5% to about 15% by weight of the topical skincare composition, of a humectant. Humectants are substances which provide the skin with water-retention benefits. Humectants have an affinity to hydrogen bonds of water molecules and to skin hydrophilic molecular functionalities, and accordingly bind themselves to internal water molecules as well as skin molecules, holding water to the outside surface and upper layers of the stratum corneum, thereby increasing the overall content in the skin itself. Topical application of cosmetic products containing humectants, (for example, glycerin) can be associated with improvements in barrier function, increases in epidermal thickness, and improvements in general skin appearance.

The topical skincare composition may comprise a humectant selected from the group consisting of polyhydric alcohols, amino acids and derivatives thereof such as proline and arginine aspartate, 1,3-butylene glycol, propylene glycol and water and codium tomentosum extract, collagen amino acids or peptides, creatinine, diglycerol, biosaccharide gum-1, glucamine salts, glucuronic acid salts, glutamic acid salts, polyethylene glycol ethers of glycerin (e.g., glycereth 20), glycerin, glycerol monopropoxylate, glycogen, hexylene glycol, honey, and extracts or derivatives thereof, hydrogenated starch hydrolysates, hydrolyzed mucopolysaccharides, inositol, keratin amino acids, glycosaminoglycans, methoxy PEG-10, methyl gluceth-10, methyl gluceth-20, methyl glucose, 3-methyl-1,3-butanediol, N-acetyl glucosamine salts, polyethylene glycol and derivatives thereof (such as PEG-15 butanediol, PEG-4, PEG-5 pentaerythitol, PEG-6, PEG-8, PEG-9), pentaerythitol, 1,2 pentanediol, PPG-1 glyceryl ether, PPG-9,2-pyrrolidone-5-carboxylic acid and its salts such as glyceryl pca, saccharide isomerate, sericin, silk amino acids, sodium acetylhyaluronate, sodium hyaluronate, sodium poly-aspartate, sodium polyglutamate, sorbeth 20, sorbeth 6, sugar and sugar alcohols and derivatives thereof such as glucose, mannose and polyglycerol sorbitol, trehalose, triglycerol, trimethyolpropane, tris (hydroxymethyl) amino methane salts, and yeast extract, and mixtures thereof.

Nonlimiting examples of polyhydric alcohols may include glycerin, diglycerin, glycerol, erythritol, arabitol, xylitol, ribitol, mannitol, sorbitol, galactitol, fucitol, maltitol, mannose, inositol, triethyleneglycol, sodium pyrrolidone carboxylic acid (PCA), zinc PCA and derivatives and mixtures thereof.

Additional Optional Skincare Composition Components

A wide variety of optional skincare composition components may further be included in the topical skincare compositions. For example, the topical skincare composition may comprise a skincare composition component selected from the following absorbents, abrasives, anticaking agents, antifoaming agents, propellants, antimicrobial agents, external analgesics, binders, biological additives, buffering agents, bulking agents, chemical additives, cosmetic biocides, denaturants, cosmetic astringents, drug astringents, film formers, opacifying agents, fragrances, pigments, colorings, essential oils, skin soothing agents, pH adjusters, plasticizers, preservative enhancers, reducing agents, additional skin-conditioning agents, skin penetration enhancing agents, skin protectants, solvents, suspending agents, solubilizing agents, sunscreens, peptides (e.g., peptides containing ten or fewer amino acids, their derivatives, isomers, and complexes with other species such as metal ions), ultraviolet light absorbers or scattering agents, tanning agents, antioxidants and/or radical scavengers, chelating agents, acute powders, oil/sebum control agents, sweat control agents, sequestrants, anti-acne agents, anti-inflammatory agents, anti-androgens, depilation agents, sugar amines (e.g., N-acetyl-glucosamine, desquamation agents/exfoliants, oil control agents, anti-cellulite actives, skin lightening agents, flavonoids, protease inhibitors (e.g., hexamidine and derivatives), non-vitamin antioxidants and radical scavengers, anti-wrinkle actives, anti-atrophy actives, minerals, phytosterols and/or plant hormones, tyrosinase inhibitors, N-acyl amino acid compounds, moisturizers, organic hydroxy acids, vitamins and derivatives thereof, natural or plant extracts, such as *Avena* (oat) extract, ceramides, and mixtures thereof. Suitable actives are further described in U.S. Publication Nos. US2006/0275237 A1 to Bissett et al., filed Apr. 21, 2006, and US2004/0175347 A1 to Bissett, filed Mar. 4, 2003. It is noted that one skilled in the art may recognize that an ingredient may have more than one function.

Anti-Inflammatory Agents

The topical skincare composition may comprise a safe and effective amount of an anti-inflammatory agent, preferably from about 0.1% to about 10%, more preferably from about 0.5% to about 5%, by weight of the topical skincare composition. The anti-inflammatory agent may improve the skin appearance benefits of the present disclosure, e.g., such agents contribute to a more uniform and acceptable skin tone or color. The exact amount of anti-inflammatory agent to be used in the compositions will depend on the particular anti-inflammatory agent utilized since such agents vary widely in potency. The anti-inflammatory agent may be selected from the group consisting of non-steroidal anti-inflammatory agents, naturally derived anti-inflammatory agents, and mixtures thereof. Nonlimiting examples of non-steroidal anti-inflammatory agents may include: oxicams (e.g., piroxicam, isoxicam, tenoxicam, and sudoxicam), salicylates (e.g., aspirin, disalcid, benorylate, trilisate, safapryn, solprin, diflunisal, and fendosal); acetic acid derivatives (e.g., diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac); fenamates (e.g., mefenamic, meclofenamic, flufenamic, niflumic, and tolfenamic acids), propionic acid derivatives (e.g., ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic); and pyrazoles (e.g., phenylbutazone, oxyphenbutazone, feprazone, azapropazone, and trimethazone). Mixtures of these non-steroidal anti-inflammatory agents may also be employed, as well as the dermatologically acceptable salts and esters of these agents.

Naturally derived anti-inflammatory agents may suitably be obtained as an extract by suitable physical and/or chemical isolation from natural sources (e.g., plants, fungi, by-products of microorganisms) or can be synthetically prepared. Nonlimiting examples of naturally derived anti-inflammatory agents may include: candelilla wax, bisabolol (e.g., alpha bisabolol), aloe vera, plant sterols (e.g., phytosterol), Manjistha (extracted from plants in the genus *Rubia*, particularly *Rubia cordifoha*), and Guggal (extracted from plants in the genus *Commiphora*, particularly *Commiphora mukul*), kola extract, chamomile, red clover extract, and sea whip extract, may be used. Additional anti-inflammatory agents useful herein may include compounds of the licorice (the plant genus/species *Glycyrrhiza glabra*) family, including glycyrrhetic acid, glycyrrhizic acid, and derivatives thereof (e.g., salts and esters). Suitable salts of the foregoing compounds may include metal and ammonium salts. Suitable esters may include $C_2$-$C_{24}$ saturated or unsaturated esters of the acids, preferably $C_{10}$-$C_{24}$, more preferably $C_{16}$-$C_{24}$. Nonlimiting examples of the foregoing may include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate.

Vitamins and Derivatives Thereof

The topical skincare composition may comprise a safe and effective amount of one or more vitamins and derivatives thereof. Nonlimiting examples of vitamins and derivatives thereof may include B3 compounds such as niacinamide, niacinnicotinic acid, tocopheryl nicotinate; B5 compounds, such as panthenol; vitamin A compounds and natural and/or synthetic analogs of Vitamin A, including retinoids, retinol, retinyl acetate, retinyl palmitate, retinoic acid, retinaldehyde, retinyl propionate, carotenoids (pro-vitamin A); vitamin E compounds, or tocopherol, including tocopheryl sorbate, tocopheryl acetate; vitamin C compounds, including ascorbate, ascorbyl esters of fatty acids, and ascorbic acid derivatives such as magnesium ascorbyl phosphate and sodium ascorbyl phosphate, ascorbyl glucoside, and ascorbyl sorbate), and derivatives of any of the aforementioned actives. The term "derivative" as used herein refers to structures which are not shown but which one skilled in the art would understand are variations of the basic compound.

Skin Soothing Agents

The topical skincare composition may comprise a safe and effective amount of a skin soothing agent, preferably from about 0.1% to about 30%, more preferably from about 0.5% to about 20%, more preferably from about 0.5% to about 10%, by weight of the topical skincare composition. Nonlimiting examples of skin soothing agents suitable for use herein may include panthenoic acid derivatives (including panthenol, dexpanthenol, ethyl panthenol), aloe vera, allantoin, bisabolol, dipotassium glycyrrhizinate, bisabolol, pentylene glycol, 4-t-butylcyclohexanol, PEG-40 hydrogenated castor oil, hydroxyphenyl propamidobenzoic acid, trideceth-9, propylene glycol, *Zingiber officinale* (ginger) root extract, and mixtures thereof. Additional examples of suitable commercially available skin soothing agents include SymSitive® (pentylene glycol, 4-t-butylcyclohexanol); SymCare® (pentylene glycol (and) 4-t-butylcyclohexanol (and) PEG-40 hydrogenated castor oil (and) trideceth-9 (and) hydroxyphenyl propamidobenzoic acid (and) propylene glycol); and SymRelief® (bisabolol (and) *Zingiber officinale* (ginger) root extract), all made available by Symrise, Holzminden, Germany).

Acute Powders

The topical skincare composition may comprise a safe and effective amount of an acute powder, preferably from about 0.01% to about 10%, preferably from about 0.05% to about 5%, by weight of the topical skincare composition. Acute powders may modify the optics and/or the feel of the composition product on the skin, such as reducing sticky and/or greasy feel. Acute powders are insoluble powders, generally from about 0.2 to about 40 microns in size. Nonlimiting examples of acute powders may include microthenes, hydrophobic starch particles (e.g., aluminum starch octenylsuccinate, tapioca starch), silicone beads (e.g., polymethylsilsesquioxane), titanium dioxide, beads, and inference pigments. Preferred acute powders may comprise tapioca starch, polymethylsilsesquioxane, or mixtures thereof.

Chelators or Chelating Agents

The topical skincare composition may comprise a safe and effective amount of a chelator or chelating agent, preferably from about 0.1% to about 10%, more preferably from about 1% to about 5%, by weight of the topical skincare composition. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage.

Propellants

Wherein the topical skincare composition is in the product form of an aerosol, the composition may comprise a propellant. Aerosols are typically applied to the skin as a spray-on product. Aerosols and other spray-on products may be useful in providing broader ranges of coverage of the topical skincare composition in a shorter amount of time than it would take for a user to apply a cream or lotion. Additionally, aerosols and other spray-on products generally allow for the user to apply the topical skincare composition without having to utilize the fingers and/or any useful spreading tools (such as, for example, towels, wipes, tissues, and the like) to spread the topical skincare composition onto the skin, minimizing risk of contaminating the affected situs with any additional bacteria from the fingers and/or spreading tools and minimizing clean-up for the user of the fingers and/or spreading tools.

Viscosity and pH of the Topical Skincare Composition

The viscosity and pH of the topical skincare composition of the present disclosure may depend on the type or form of product form desired for the composition. Generally, the topical skincare composition may have a viscosity of from about 30,000 cP to about 300,000 cP when measured according to the Viscosity Test Method described herein. The viscosity of the composition as used herein is described as the Brookfield viscosity.

Nonlimiting exemplary topical skincare compositions of the present disclosure wherein the composition is in the form of a lotion may have a viscosity of from about 30,000 cP to about 100,000 cP. Nonlimiting exemplary topical skincare compositions of the present disclosure wherein the composition is in the form of a cream may have a viscosity of from about 50,000 cP to about 300,000 cP. Nonlimiting exemplary topical skincare compositions of the present disclosure wherein the composition is in the form of a serum may have a viscosity of from about 10,000 cP to about 30,000 cP. Viscosity is measured according to the Viscosity Test Method as described herein.

The topical skincare compositions of the present disclosure are preferably formulated to have a pH of 10.5 or below. The pH values of these compositions preferably range from about 2 to about 10.5, more preferably from about 3 to about 8, even more preferably from about 4 to about 7. pH is measured according to the pH Test Method as described herein.

Methods of Making Topical Skincare Compositions

The topical skincare compositions of the present disclosure may be generally prepared by conventional methods such as are known in the art of making topical compositions. Such methods typically involve mixing of the ingredients in one or more steps to a relatively uniform state, with or without heating, cooling, application of vacuum, and the like. Typically, emulsions may be prepared by first mixing the aqueous phase materials separately from the fatty phase materials and then combining the two phases as appropriate to yield the desired continuous phase. The compositions may preferably be prepared such as to optimize stability (e.g., physical stability, chemical stability) and/or delivery of the active materials.

Methods of Using Topical Skincare Compositions

Topical skincare compositions of the present disclosure may be used to treat symptoms of itch, redness, flaking, dryness, and/or roughness of the skin, scalp, and/or mucous membrane. The treatment method may include the steps of providing a topical skincare composition according to the present disclosure and applying a safe and effective amount of the topical skincare composition to at least a portion of a user's skin, scalp, and/or mucous membrane in need thereof.

The itch, redness, flaking, dryness, and/or roughness may be associated with at least one skin, scalp, and/or mucous membrane condition selected from the group consisting of eczematous dermatitis, contact dermatitis, atopic dermatitis, and psoriasis. Other conditions wherein itching, redness, flaking, dryness, and/or roughness may be experienced are also contemplated. The topical skincare composition may also be applied to the skin in need thereof, including but not limited to the affected situs, the surrounding skin, and generally the skin all over the body, when there are active flares present as well as when there are no active flares present. The portion of the user's skin, scalp, and/or mucous membrane in need thereof may be presently affected by one or more of the following: rash, scaling, lesions, fissures, and/or bumps, or, none of the above may be present. The term "skin, scalp, and/or mucous membrane in need thereof", is meant to be construed as narrowly as the affected situs where itch, redness, flaking, dryness, and/or roughness is present and/or where an active flare is present to as broadly as the skin of the body as a whole. The topical skincare composition may provide the benefit of relief, preferably fast relief, of itch, redness, flaking, dryness, and/or roughness as well as other bothersome symptoms associated with eczematous dermatitis, contact dermatitis, atopic dermatitis, and/or psoriasis during active flares. By "relief", it is meant that the user may feel relief or improvement of the symptoms after applying the topical skincare composition. By "fast relief", it is meant that the user may feel relief or improvement of the symptoms immediately after applying the topical skincare composition, within one about (1) day after applying the topical skincare composition, within about four (4) days after applying the topical skincare composition, within about one (1) week after applying the topical skincare composition, within about two (2) weeks after applying the topical skincare composition, within about four (4) weeks after applying the topical skincare composition, within about eight (8) weeks after applying the topical skincare composition, and so on, generally less than about twelve (12) weeks after applying the topical skincare composition. Preferably, the topical skincare composition may provide the benefit of fast relief of itch, redness, flaking, dryness, and/or roughness as well as other bothersome symptoms associated with eczematous dermatitis, contact dermatitis, atopic dermatitis, and/or psoriasis during active flares within one (1) to seven (7) days after applying the topical skincare application.

The method may include the step of providing a topical skincare composition according to the present disclosure. The topical skincare composition may be in any product form that enables a user to apply the composition to the user's skin, scalp, and/or mucous membrane. Examples include, but are not limited to, the product forms as disclosed herein. The topical skincare composition may be provided in a vessel depending upon the product form, such as for example, in ajar, in a squeeze tube, in a bottle, in a canister, or any such vessel known to one skilled in the art to deliver topical skincare compositions.

Many regimens exist for the application of topical skincare compositions. The step of applying a safe and effective amount of the topical skincare composition to at least a portion of a user's skin, scalp, and/or mucous membrane in need thereof may be performed, by way of nonlimiting example, as follows. A user may obtain the provided topical skincare composition and apply a liberal amount of the topical skincare composition to the skin, scalp, and/or mucous membrane in need thereof, preferably with even more liberal application any affected situses and area surrounding the affected situses. The step of applying the topical skincare composition to the portion of the user's skin, scalp, and/or mucous membrane in need thereof may comprise applying from about 0.01 g/m$^2$ to about 20 g/m$^2$, or from about 0.05 g/m$^2$ to 15 g/m$^2$, or from about 0.1 g/m$^2$ to about 10 g/m$^2$ of the topical skincare composition.

In a nonlimiting example, the step of applying the topical skincare composition to the portion of the user's skin, scalp, and/or mucous membrane in need thereof is repeated at least once, preferably at least twice, or on a more frequent basis, within a twenty-four-hour time period. When applied twice daily, the first and second applications may be separated by at least 1 to 12 hours. Typically, the topical skincare composition may be applied in the morning and/or in the evening before bed.

The step of applying the topical skincare composition may be repeated during a treatment period. The treatment period is ideally of sufficient time to provide a relief or improvement of itch, redness, flaking, dryness, and/or roughness and to also improve skin health. The treatment period may be up until the user experiences relief or improvement in itch, redness, flaking, dryness, and/or roughness, but preferably the treatment period continues even after the user experiences relief or improvement in itch, redness, flaking, dryness, and/or roughness so that the topical skincare composition may gradually improve the health of the skin. Long-term application of the topical skincare composition after the user experiences relief or improvement of challenged skin symptoms may potentially lessen the frequency and/or severity of future occurrences of challenged skin symptoms. The treatment period may be at least 2 consecutive days, at least 3 consecutive days, at least 4 consecutive days, at least 5 consecutive days, at least 6 consecutive days, at least 1 week, at least 2 weeks, at least 3 weeks, at least 4 weeks, at least 5 weeks, at least 6 weeks, at least 7 weeks, at least 8 weeks, and so on. The treatment period may extend over multiple months (i.e., 3-12 months) or multiple years. In a nonlimiting example, the topical skincare composition may be applied at least once, preferably at least twice, a day during a treatment period of at least 1 week, about 2 weeks, about 3 weeks, or about 4 weeks. The topical skincare composition may be concurrently applied in addition to any other prescription and/or non-prescription compositions the user may be taking.

In a nonlimiting example, after application of the topical skincare composition to the user's skin, scalp, and/or mucous membrane in need thereof, the topical skincare composition is not removed for at least five minutes. Applicant has found that even leaving the topical skincare composition without removal for at least five minutes may provide some relief or improvement of itch, redness, flaking, dryness, and/or roughness of the skin, scalp, and/or mucous membrane. Preferably, the topical skincare composition is not removed for at least thirty minutes, more preferably for at least one hour, even more preferably for at least several hours, or until the next application of the topical skincare composition. In applications such as when the topical skincare composition is used for the scalp as a rinse-off product, it is particularly beneficial for the topical skincare composition to not be removed for at least five minutes. A user may cleanse the skin, scalp, and/or mucous membrane prior to application of the topical skincare composition such as by using a bar of soap or other conventional cleansers. A user may apply the topical skincare composition without cleansing the skin, scalp, and/or mucous membrane prior to application. After applying the topical skincare composition, a user may occlude the topical skincare composition with, for example, a bandage. Occluding with a bandage may keep the topical skincare composition from being rubbed off of the skin, scalp, and/or mucous membrane by external objects, allowing for longer exposure of the skin, scalp, and/or mucous membrane to the composition.

Test Methods

Viscosity Test Method

The viscosity of samples can be measured using a standard viscometer, such as, for example, a Brookfield DV2T viscometer (manufactured by Brookfield Ametek, Middleboro, Massachusetts, U.S.A.), fitted with a helipath T-bar spindle type T-C. The viscometer is leveled, setup and calibrated according to the manufacturer's standards. The viscometer speed (RPM) is selected to ensure the measured viscosity is within the manufacturer's recommended settings (e.g., 5 RPM).

Samples are stored in sealed glass jars with an opening and internal diameter of at least 40 mm and filled to a height of at least 50 mm with care taken to avoid entrapped air bubbles. Centrifugation may be used to help removed entrained air. Sample jars are equilibrated at 23° C.±2° C. and about 50%±2% relative humidity for at least 24 hours prior to measurement.

Viscosity is measured at 23° C.±2° C. and about 50%±2% relative humidity by placing the uncapped sample jar under the viscometer and lowering the viscometer until the tip of the T-bar touches the surface of the sample. The descending helipath is turned on and a timer started once the cross-bar of the T-bar touches the surface of the sample. A reading is taken about every 10 seconds over the time period of between about 45 seconds and about 1 minute. The viscosity is calculated as the arithmetic average of the viscosities recorded. Care is taken to ensure the T-bar does not touch the glass jar.

pH Test Method pH can be using a standard pH meter such as, for example, a Beckman Coulter model PHI1410 pH meter equipped with a general-purpose probe (manufactured by Beckman Coulter, Brea, California, U.S.A.). The pH meter is calibrated according to the manufacturer's instructions. Measurements are performed after storing the compositions at room temperature (approximately 23° C.±2° C.) for approximately 24 hours.

PGE2 Assay

Inhibiting the Cell's Inflammation Response to a Stressor—Prostaglandin E2 ("PGE2") Assay The following assay may be used to estimate the generation of PGE2 in-vitro. PGE2 is a hormone-like substance that is known to participate in modulation of inflammation. Cellular inflammation is associated with a variety of hair, skin and scalp conditions, and thus inhibiting PGE2 activation vis-à-vis cellular inflammation may help treat these types of hair, skin and scalp conditions.

Method

Tert keratinocytes ("tKC"—tKCs are human keratinocytes that have been transfected with DNA adding telomerase to immortalize the cells) are plated at 40,000 cells/well into 24-well plates in 1 ml/well volume. EpiLife Medium (Life Technologies cat #MEPICFPRF500) supplemented with keratinocyte growth supplement (Life technologies cat #S-001-5) is used as the assay media. The cells are grown to confluence/near confluence, and then subjected to 15 mJ/cm$^2$ UVB-stress. The test compositions and a positive control (10 uM idebenone) are added, and the plates are incubated for 18-24 hours. The supernatant is removed from each well, and the cells are rinsed with 2 ml/well medium (without supplements). A Cell Titer-Glo assay (Promega cat #G7571; Madison WI), which measures ATP activity, is conducted on the cells for normalization. The supernatant is tested in a PGE2 assay (Prostaglandin E2 Assay kit from Cisbio Bioassays cat #62P2APEB) according to the manufacturer's instructions. The PGE2 results are normalized to ATP activity. The PGE2 quantitation (pg/mL) from the supernatant is divided by the normalization factor (treatment ATP/control ATP).

Sample Calculation
    Luminescence of vehicle control in ATP assay=100
    Luminescence of test treatment in ATP assay=90
    Normalization factor for test treatment=0.9
    PGE2 quantitation for vehicle control=2000 pg/mL PGE2
    PGE2 quantitation for test treatment=1600 pg/mL PGE2
    Normalized PGE2 Values
        control=2000/1=2000
        test=1600/0.9=1778

% inhibition for test=[100×(2000−1778)/2000]
=11.1%

EXAMPLES

The following data and examples are provided to help illustrate the topical skincare compositions described herein. The exemplified compositions are given solely for the purpose of illustration and are not to be construed as limitations of the present disclosure, as many variations thereof are possible without departing from the spirit and scope of the disclosure. All parts, percentages, and ratios herein are by weight unless otherwise specified.

Example 1: PGE2 Inhibition of Ingredients of Topical Skincare Compositions

This example demonstrates the ability of *Centella asiatica* Selected Triterpenes (CAST) extract in combination with *Populas alba* bark extract and/or *Vincetoxicum officinale* root extract to inhibit PGE2 activation in a synergistic manner. Analysis of the effects of *Centella asiatica* Selected Triterpenes (CAST), a *Populas alba* bark extract, *Vincetoxicum officinale* root extract, a combination of CAST and a *Populas alba* bark extract (1:1 weight ratio), a combination of CAST and *Vincetoxicum officinale* root extract (1:1 weight ratio), and a combination of CAST, a *Populas alba* barl extract, and *Vincetoxicum officinale* root extract (1:1:1 weight ratio) on skin irritancy using the inflammatory mediator Prostaglandin E2 (PGE2) is run according to the PGE2 Assay as described herein.

The general plate layout in these experiments is as exemplified below for white poplar (the same layout is used for *Vincetoxicum*):

| media control | CAST | White Poplar | CAST + White Poplar | idebenone (positive control) | White Poplar |
|---|---|---|---|---|---|
| media control | CAST | White Poplar | CAST + White Poplar | idebenone (positive control) | White Poplar |
| media control | CAST | White Poplar | CAST + White Poplar | idebenone (positive control) | CAST + White Poplar |
| media control | CAST | White Poplar | CAST + White Poplar | idebenone (positive control) | CAST + White Poplar |

Therefore, for the white poplar experiments, n=4 for CAST on each plate, n=6 for white poplar, n=6 for combination.

Also, for the *vincetoxicum* experiments n=4 for CAST on each plate, n=6 for *Vincetoxicum*, n=6 for combination.

The results of the PGE2 Assay are summarized in Table 1 below, which shows the percent inhibition for *Centella asiatica* Selected Triterpenes (CAST) extract, *Populas alba* bark extract, *Vincetoxicum officinale* root extract, a combination of CAST extract and *Populas alba* bark extract (1:1 weight ratio), a combination of CAST extract and *Vincetoxicum officinale* root extract (1:1 weight ratio), and a combination of CAST extract, *Populas alba* bark extract, and *Vincetoxicum officinale* root extract (1:1:1 weight ratio). Percent inhibition is calculated as described above in the sample calculation. Positive percent inhibition values indicate a decrease in PGE2 production and negative percent inhibition values indicate an increase in PGE2 production, which correlates to increased inflammation.

Student's T-Test (equal variance, 2 sided) is used to calculate p-values between observed combinations and expected combinations with p-value<0.05 considered statistically significant. Expected combination values are calculated by adding the individual observed PGE2 inhibition values: CAST inhibition value+white poplar inhibition value; CAST inhibition value+*Vincetoxicum* inhibition value; CAST inhibition value+white poplar inhibition value+*Vincetoxicum* inhibition value. The data suggests that the combination of these materials reduces skin irritation and itch.

TABLE 1

Summary of PGE2 Assay Data (weight ratio of 1:1 or 1:1:1)

| CAST[1] [w/w %] | White Poplar[2] [w/w %] | Vincetoxicum officinale[3] [w/w %] | PGE2 inhibition Observed Values | p-value observed vs expected |
|---|---|---|---|---|
| 0.0001% | 0% | 0% | 5.9 | |
| 0% | 0.000011% | 0% | −10.5 | |
| 0% | 0% | 0.000011% | −40.3 | |
| 0.0001% | 0.000011% | 0% | 69.3 | 0.0034 |
| 0.0001% | 0% | 0.000011% | 72.2 | 0.00076 |
| 0.0001% | 0.000011% | 0.000011% | 56.9 | 0.013 |

[1]Centella Asiatica Selected Triterpenes (CAST), having ≥ 36.0% ≤ 44.0% of asiaticoside, ≥ 56% ≤ 64.0% of genins as a sum of asiatic acid and madecassic acid) made commercially available by Indena (Milan, Italy) as a 100 w/w % active dry powder.

[2]White Poplar bark Extract expressed as active w/w % is supplied as a 12.5% active solution in 60% ethanol/40% water solvent, by Spaus, Inc. (Suite 460, Oklahoma City, OK 73104).

[3]Vincetoxicum officinale root extract expressed as active w/w % is supplied as a 12.5% active solution in 60% ethanol/40% water solvent, by Spaus, Inc. (Suite 460, Oklahoma City, OK 73104).

As shown in Table 1, individually CAST, white poplar, and *Vincetoxicum officinale* provide a limited benefit or no benefit. However, the combination of CAST+white poplar (9:1), CAST+*Vincetoxicum officinale* (9:1), and CAST+White Poplar+*Vincetoxicum officinale* (9:1:1) provide a synergistic reduction in release of PGE2. The results demonstrate that the combination of CAST+white poplar, CAST+*Vincetoxicum officinale*, or CAST+White Poplar+*Vincetoxicum officinale* reduce release of PGE2. The data suggests that the combination of CAST+white poplar (9:1), CAST+*Vincetoxicum officinale* (9:1), and CAST+White Poplar+*Vincetoxicum officinale* (9:1:1) reduce skin irritation and itch.

TABLE 2

Summary of PGE2 Inhibition Data (different weight ratios of CAST to *Vincetoxicum officinale* on an active basis). CAST level fixed at 0.0001% w/w.

| Vincetoxicum officinale [w/w %] | CAST: Vincetoxicum officinale weight ratio | PGE2 inhibition Observed Values [CAST alone] | PGE2 inhibition Observed Values [Vincetoxicum officinale alone] | PGE2 inhibition Expected Values CAST + Vincetoxicum officinale | PGE2 inhibition Observed Values CAST + Vincetoxicum officinale | Synergy Delta positive number indicates potential synergy | p-value expected vs observed |
|---|---|---|---|---|---|---|---|
| 0.0011% | 1:11 | 6.6 | −10.0 | −3.4 | −23.4 | −19.9 | 0.079055 |
| 0.00011% | 1:1.1 | 6.6 | −23.5 | −16.9 | 1.6 | 18.4 | 0.076372 |
| 0.000056% | 1.8:1 | 6.6 | −30.0 | −23.4 | 53.2 | 76.6 | 0.00011 |
| 0.000022% | 4.5:1 | 6.6 | −35.5 | −28.9 | 58.4 | 87.3 | 8.96E−05 |
| 0.000011% | 9.0:1 | 6.6 | −40.3 | −33.7 | 71.3 | 105.0 | 5.93E−05 |
| 0.0000056% | 18:1 | 6.6 | −16.7 | −10.1 | 54.4 | 64.5 | 0.000111 |
| 0.0000022% | 45:1 | 6.6 | −5.8 | 0.8 | 3.1 | 2.3 | 0.217866 |
| 0.0000011% | 90:1 | 6.6 | −9.5 | −2.9 | −2.6 | 0.3 | 0.361381 |
| 0.00000011% | 900:1 | 6.6 | 1.4 | 8.0 | −0.4 | −8.3 | 0.80183 |

TABLE 3

Summary of PGE2 Inhibition Data (different weight ratios of CAST to white poplar on an active basis). CAST level fixed at 0.0001% w/w.

| White Poplar [w/w %] | CAST: white poplar weight ratio | PGE2 inhibition Observed Values [CAST alone] | PGE2 inhibition Observed Values [White Poplar alone] | PGE2 inhibition Expected Values [CAST + White Poplar] | PGE2 Inhibition Observed [CAST + White Poplar] | Synergy Delta positive number indicates potential synergy | p-value expected vs observed |
|---|---|---|---|---|---|---|---|
| 0.001112%    | 1:11  | 3.5 | −28.5 | −25.0 | −27.1 | −2.0 | 0.618197 |
| 0.000222%    | 1:2.2 | 3.5 | 0.3   | 3.8   | 16.0  | 12.2 | 0.201473 |
| 0.000111%    | 1:1.1 | 3.5 | −10.2 | −6.7  | 78.0  | 84.7 | 8.99E−06 |
| 0.000011%    | 9:1   | 3.5 | −10.4 | −6.9  | 79.4  | 86.3 | 1.75E−05 |
| 0.0000011%   | 90:1  | 3.5 | −2.4  | 1.1   | 67.4  | 66.3 | 0.000341 |
| 0.00000056%  | 180:1 | 3.5 | 12.2  | 15.7  | 19.5  | 3.8  | 0.200084 |
| 0.00000011%  | 900:1 | 3.5 | 10.6  | 14.1  | 16.5  | 2.4  | 0.266766 |

As shown in Table 2, the combination of CAST+*Vincetoxicum officinale* in selected ratios reduces release of PGE2, an inflammatory mediator. The data suggests that the combination of these materials in selected ratios reduces skin irritation and itch.

As shown in Table 3, the combination of CAST+white poplar in selected ratios reduces release of PGE2, an inflammatory mediator. The data suggests that the combination of these materials in selected ratios reduces skin irritation and itch.

Example 2: Examples of Topical Skincare Compositions

TABLE 4

Topical Skincare Compositions, mass %

| Ingredient | Test Composition 1 | Comparative Composition 1 | Comparative Composition 2 | Comparative Composition 3 |
|---|---|---|---|---|
| Carrier[1] | Balance | Balance | Balance | Balance |
| Humectant[2] | 10.000 | 10.000 | 10.000 | 10.000 |
| Skin soothing agent[3] | 1.000 | 1.000 | 1.000 | 1.000 |
| Chelant[4] | 0.100 | 0.100 | 0.100 | 0.100 |
| pH adjustor[5] | 0.022 | 0.022 | 0.022 | 0.022 |
| Emollient[6] | 4.100 | 4.100 | 4.100 | 4.100 |
| Vitamins and derivatives thereof[7] | 0.600 | 0.600 | 0.600 | 0.600 |
| Emulsifier/surfactant[8] | 0.400 | 0.200 | 0.200 | 0.200 |
| Structuring Agent[9] | 1.580 | 1.580 | 1.580 | 1.580 |
| Avena (oat) oil extract[10] | 1.000 | 0.000 | 1.000 | 0.000 |
| Vincetoxicum officinale extract[11] | 0.003 | 0.000 | 0.050 | 0.000 |
| Thickening agent[12] | 2.300 | 2.300 | 2.300 | 2.300 |
| Centella Asiatica extract[13] | 0.006 | 0.000 | 0.000 | 0.006 |
| Preservative[14] | 0.375 | 0.000 | 0.000 | 0.375 |
| Carrier[1] | 0.050 | 0.000 | 0.000 | 0.050 |
| Preservative[14] | 0.000 | 0.375 | 0.375 | 0.000 |
| Emollient[15] | 1.000-1.140 | 1.140 | 1.000 | 1.14 |
| White poplar extract[16] | 0.0012 | 0.000 | 0.500 | 0.000 |
| Acute Powder[17] | 2.000 | 2.000 | 2.000 | 2.000 |
| Total | 100 | 100 | 100 | 100 |

Raw Materials for Table 4
[1] United States Pharmacopeia (USP) Purified Water Wash.
[2] Glycerin EP
[3] Dexpanthenol
[4] Disodium EDTA
[5] Sodium hydroxide
[6] Isopropyl isostearate, caprylic/capric triglycerides, petrolatum.
[7] DL-alpha Tocopheryl acetate (Vitamin E)
[8] Cetearyl glucoside and cetearyl alcohol, polyethylene glycol (PEG) 100 stearate, stearic acid.
[9] Stearyl alcohol, cetyl alcohol 95%, behenyl alcohol 75%
[10] AVENALIPID ® supplied by Symrise, Inc. (Holzminden, Germany).
[11] Vincetoxicum officinale root extract, Spaus, Inc. (Suite 460, Oklahoma City, OK 73104) added as 12.5 w/w % active solution in 60% ethanol/40% water solvent.
[12] Caprylic/capric triglycerides and sodium acrylates copolymer.
[13] Centella Asiatica Selected Triterpenes (CAST) supplied by Indena (Milan, Italy). HPLC content: ≥ 36.0% ≤ 44.0% of asiaticoside, ≥ 56% ≤ 64% of genins as a sum of asiatic acid and madecassic acid. Form: white powder. Solubility: soluble in propylene glycol, ethoxydiglycol, polyethyleneglycol 600, polyoxyethylene sorbitan monooleate.
[14] Phenoxyethanol NF.
[15] Dimethicone and dimethiconol.
[16] White Poplar bark extract, Spaus, Inc. (Suite 460, Oklahoma City, OK 73104 added as 12.5 w/w % active solution in 60% ethanol/40% water solvent.
[17] Tapioca starch (and) polymethylsilsesquioxane starch is a non-GMO, aluminum free, modified tapioca starch commercially available under the tradename DRY-FLO ® TS as sold by AkzoNobel (Amsterdam, Netherlands).

Combinations:
A. A topical skincare composition comprising: a *Centella asiatica* extract;
 a *Populas alba* extract, preferably a *Populas alba* bark extract; and a dermatologically acceptable carrier, wherein the *Centella asiatica* extract and the *Populas alba* extract are in a weight ratio of about 1:5 to about 1,000:1, preferably about 1:3 to about 200:1, more preferably about 1:2 to about 100:1, even more preferably about 1:1.1 to about 9:1.
B. A topical skincare composition comprising:
 a *Centella asiatica* extract;
 a *Vincetoxicum officinale* extract, preferably a *Vincetoxicum officinale* root extract; and
 a dermatologically acceptable carrier, wherein the *Centella asiatica* extract and the *Vincetoxicum officinale* extract are in a weight ratio of about 1:2 to about 100:1, preferably about 2:1 to about 20:1, more preferably about 4.5:1 to about 9:1.

C. A method of treating symptoms of itch, redness, flaking, dryness, and/or roughness of the skin, scalp, and/or mucous membrane, the method comprising the steps of: providing a topical skincare composition comprising a *Centella asiatica* extract in combination with a *Vincetoxicum officinale* extract, preferably a *Vincetoxicum officinale* root extract, and/or a *Populas alba* extract, preferably a *Populas alba* bark extract, and a dermatologically acceptable carrier; and applying a safe and effective amount of the topical skincare composition to at least a portion of a user's skin, scalp, and/or mucous membrane in need thereof.

D. The method of treating symptoms of itch, redness, flaking, dryness, and/or roughness of the skin, scalp, and/or mucous membrane according to paragraph C, wherein the symptoms of itch, redness, flaking, dryness, and/or roughness are associated with at least one skin, scalp, and/or mucous membrane condition selected from the group consisting of eczematous dermatitis, contact dermatitis, atopic dermatitis, and psoriasis.

E. The method of treating symptoms of itch, redness, flaking, dryness, and/or roughness of the skin, scalp, and/or mucous membrane according to paragraphs C or D, wherein the step of applying the topical skincare composition to the portion of the user's skin, scalp, and/or mucous membrane in need thereof comprises applying from about 0.01 g/m$^2$ to about 20 g/m$^2$ of the topical skincare composition.

F. The method of treating symptoms of itch, redness, flaking, dryness, and/or roughness of the skin, scalp, and/or mucous membrane according to paragraphs C, D, or E, wherein the step of applying the topical skincare composition to the portion of the user's skin, scalp, and/or mucous membrane in need thereof is repeated at least once within a twenty-four-hour time period repeated for 4 consecutive days.

G. The method of treating symptoms of itch, redness, flaking, dryness, and/or roughness of the skin, scalp, and/or mucous membrane according to paragraphs C, D, E, or F, wherein the topical skincare composition is not removed from the portion of the user's skin, scalp, and/or mucous membrane in need thereof for at least five minutes after the step of applying a safe and effective amount of the topical skincare composition to the portion of the user's skin, scalp, and/or mucous membrane in need thereof.

H. The topical skincare composition according to paragraph A, wherein the composition further comprises a *Vincetoxicum officinale* extract.

I. The topical skincare composition according to any one of the preceding paragraphs, wherein the composition comprises at least 0.00001% by weight of the composition, of *Centella asiatica* extract.

J. The topical skincare composition according to any one of the preceding paragraphs, wherein the *Centella asiatica* extract comprises two or more triterpenes selected from the group consisting of asiaticoside, asiatic acid, madecassoside, and mixtures thereof.

K. The topical skincare composition according to any one of the preceding paragraphs, wherein the *Centella asiatica* extract comprises from about 20% to about 60% by weight of the *Centella asiatica* extract, of asiaticoside and from about 40% to about 80% by weight of the *Centella asiatica* extract, of a mixture of asiatic acid and madecassic acid.

L. The topical skincare composition according to any one of the preceding paragraphs, wherein the composition comprises at least 0.000001% by weight of the composition, of *Populas alba* extract.

M. The topical skincare composition according to any one of the preceding paragraphs, wherein the composition comprises at least 0.000001% by weight of the composition, of *Vincetoxicum officinale* extract.

N. The topical skincare composition according to any one of the preceding paragraphs, wherein the topical skincare composition is substantially free of a steroid.

O. The topical skincare composition according to any one of the preceding paragraphs, wherein the dermatologically acceptable carrier comprises water.

P. The topical skincare composition according to any one of the preceding paragraphs, wherein the dermatologically acceptable carrier is an oil-in-water emulsion.

Q. The topical skincare composition according to any one of the preceding paragraphs, wherein the composition further comprises at least 0.01% by weight of the composition, of a lipid bilayer structurant.

R. The topical skincare composition according to any one of the preceding paragraphs, wherein the composition further comprises at least 0.0001% by weight of the composition, of a preservative.

S. The topical skincare composition according to any one of the preceding paragraphs, wherein the composition has a viscosity of from about 30,000 cP to about 300,000 cP, when measured according to the Viscosity Test Method described herein.

T. A topical skincare composition capable of alleviating symptoms associated with eczematous dermatitis, contact dermatitis, atopic dermatitis, and/or psoriasis, the topical skincare composition comprising a *Centella asiatica* extract in combination with a *Vincetoxicum officinale* extract and/or a *Populas alba* extract, preferably a *Vincetoxicum officinale* root extract and/or a *Populas alba* bark extract, and a dermatologically acceptable carrier.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A topical skincare composition comprising:
   a. a *Centella asiatica* solution comprising a solvent and a *Centella asiatica* extract comprising from about 36% to about 44% asiaticoside and from about 56% to about 64% of a sum of asiatic acid, madecassic acid, and genins thereof; wherein the solution comprises at least about 0.00001% by weight of the composition of the *Centella asiatica* extract;
   b. a *Vincetoxicum officinale* solution comprising *Vincetoxicum officinale* root extract and a solvent; wherein the solution comprises at least about 0.000001% of the *Vincetoxicum officinale* extract; and
   c. a dermatologically acceptable carrier;
   wherein the *Centella asiatica* extract and the *Vincetoxicum officinale* extract are in a weight ratio of about 1:1.1 to about 90:1;
   wherein the combination of *Centella asiatica* extract and *Vincetoxicum officinale* extract inhibit PGE2 activation in a synergistic manner.

2. The topical skincare composition according to claim 1, wherein the topical skincare composition is free of a steroid.

3. The topical skincare composition according to claim 1, wherein the dermatologically acceptable carrier comprises water.

4. The topical skincare composition according to claim 1, wherein the dermatologically acceptable carrier is an oil-in-water emulsion.

5. The topical skincare composition according to claim 1, wherein the composition further comprises at least about 0.01% by weight of the composition of a lipid bilayer structurant.

6. The topical skincare composition according to claim 1, wherein the composition further comprises at least about 0.0001% by weight of the composition of a preservative.

7. The topical skincare composition according to claim 1, wherein the composition has a viscosity of from about 30,000 cP to about 300,000 cP.

8. The topical skincare composition according to claim 1, wherein the *Centella asiatica* extract and the *Vincetoxicum officinale* extract are in a weight ratio of about 1.8:1 to about 18:1.

9. The topical skincare composition according to claim 1, wherein the *Centella asiatica* extract and the *Vincetoxicum officinale* extract are in a weight ratio of about 4.5:1 to about 9:1.

* * * * *